US006670374B1

(12) United States Patent
Anderson et al.

(10) Patent No.: US 6,670,374 B1
(45) Date of Patent: Dec. 30, 2003

(54) SWAINSONINE COMPOUNDS AS INHIBITORS OF TOXIN RECEPTOR EXPRESSION

(75) Inventors: Robin C. Anderson, College Station, TX (US); David J. Nisbet, Bryan, TX (US); Robert E. Droleskey, College Station, TX (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 10/166,974

(22) Filed: Jun. 11, 2002

(51) Int. Cl.$^7$ ................................................ A61K 31/44
(52) U.S. Cl. ....................................................... 514/299
(58) Field of Search .......................................... 514/299

(56) References Cited

U.S. PATENT DOCUMENTS

| | | | |
|---|---|---|---|
| 5,466,809 | A | 11/1995 | Dime |
| 5,939,279 | A | 8/1999 | Smith et al. |
| 5,962,467 | A | 10/1999 | Carver et al. |
| 6,048,870 | A | 4/2000 | Shah et al. |
| 6,051,711 | A | 4/2000 | Tropper et al. |
| 6,262,065 | B1 | 7/2001 | Pearson et al. |

FOREIGN PATENT DOCUMENTS

| | | | |
|---|---|---|---|
| EP | 0104826 | A2 * | 9/1983 |
| EP | 0295538 | A2 * | 6/1988 |

OTHER PUBLICATIONS

R.E. Droleskey et al., Modulation of *Escherichia coli* Shiga Toxin Activity on Vero Cells by the use of the Secondary Plant Compound Swainsonine, $6_{th}$ International Symposium of Poisonous Plants, Scientific Programme and Abstracts, Glasgow, Scotland, Aug. 6–10, 2001, distributed 2001.

M. Jacewicz, et al., Pathogenesis of Shigella Diarrhea. XIV. Analysis of Shiga Toxin Receptors on Cloned HeLa Cells, The Journal of Infection Diseases, vol. 159, No. 5, May 1989, pp. 881–889.

P.R. Dorling et al., Toxicants of Plant Origin, Swainsonine: A Toxic Indolizidine Alkaloid, vol. 1, Chapter 9, pp. 237–255.

Kenneth Olden et al., Practical Uses of Swainsonine in Biomedical Research, pp. 107–116.

* cited by examiner

*Primary Examiner*—Kevin E. Weddington
(74) *Attorney, Agent, or Firm*—John D. Fado; Randall E. Deck

(57) ABSTRACT

The invention provides a method for treating infections in animals which are caused by toxin-producing enteric bacterial pathogens, including Shigella species, enterohemorrhagic *E. coli*, and enterotoxigenic *E. coli*. Receptors expressed by animal cells which typically recognize these bacterial toxins may be modified by administration of swainsonine compounds to the animal, thereby effectively inhibiting toxin binding to the cells.

19 Claims, No Drawings

SWAINSONINE COMPOUNDS AS INHIBITORS OF TOXIN RECEPTOR EXPRESSION

BACKGROUND OF THE INVENTION

1. Field of the Invention

This invention relates to a process for reducing the manifestation of disease by enteric bacterial pathogens in animals using swainsonine compounds.

2. Description of the Prior Art

A number of diseases of humans and other animals are associated with the production of toxins by enteric bacteria. *Escherichia coli* O157:H7 and other shiga toxin-producing strains have recently gained widespread public attention in the United States due to their recently recognized association with two serious extraintestinal diseases in humans, hemolytic uremic syndrome (HUS) and thrombotic thrombocytopenic purpura (TTP). Worldwide, enterohemorrhagic *E. coli*, including *E. coli* O157:H7 and other shiga toxin-producing *E. coli*, are an increasingly important health problem in humans and other animals. First identified as a cause of human illness in early 1982 following two outbreaks of food-related hemorrhagic colitis in Oregon and Michigan (M. A. Karmali, 1989, Infection by Verocytotoxin-Producing *Escherichia coli*, Clin. Microbiol. Rev., 2:15–38; and L. W. Riley, et al., 1983, Hemorrhagic colitis associated with a rare *Escherichia coli* serotype, New Eng. J. Med., 308: 681–685), the reported incidence of disease associated with enterohemorrhagic *E. coli* has risen steadily, with outbreaks occurring in the United States, Canada, and Europe.

SUMMARY OF THE INVENTION

We have now discovered a method for treating infections in animals which are caused by toxin-producing enteric bacterial pathogens, including Shigella species, enterohemorrhagic *E. coli*, and enterotoxigenic *E. coli*. Receptors expressed by animal cells which typically recognize these bacterial toxins may be modified by administration of a swainsonine compound to the animal, thereby effectively inhibiting toxin binding to the cells.

In accordance with this discovery, it is an object of this invention to provide a method for treating infections caused by toxin-producing enteric bacterial pathogens.

Another object of this invention is to provide a method for treating infections of Shigella species, enterohemorrhagic *E. coli*, and enterotoxigenic *E. coli*.

Yet another object of the invention is to provide a method for treating infections caused by toxin-producing enteric bacterial pathogens which does not target the bacteria per se, such that the development of bacterial resistance is irrelevant.

Other objects and advantages of this invention will become readily apparent from the ensuing description.

DETAILED DESCRIPTION OF THE INVENTION

The invention provides a method for preventing or mitigating one or more conditions in an animal which are mediated by the toxins elicited by enteric bacterial pathogens. As described in greater detail hereinbelow, in accordance with this invention, the administration of one or more swainsonine compounds to a susceptible animal effects the modification of cell surface receptors for the toxins, thereby interfering with the binding of the toxins to the cells and reducing or preventing cell cytotoxicity. The method is effective for treating animals against infection by a number of toxin-producing enteric pathogens, including but not limited to enterotoxigenic *E. coli* (ETEC), and particularly shiga toxin-producing Shigella species and enterohemorrhagic *E. coli* such as *E. coli* O157:H7. As described by Nataro and Kaper (Diarrheagic *Escherichia coli*, Clinical Microbiology Reviews, 1998, vol. 11, no. 1, pp. 142–201, the contents of which are incorporated by reference herein) and as used herein, enterotoxigenic *E. coli* refers to *E. coli* strains that elaborate at least one of two defined groups heat labile or heat stable enterotoxins (LT or ST, respectively). In contrast, enterohemorrhagic *E. coli* refers to *E. coli* strains that produce one or more shiga toxins (also referred to as shiga-like toxins, SLTs, or verotoxins) which comprise an enzymatically active A subunit and a multimeric cell receptor binding B subunit. Infections caused by common serotypes of enterohemorrhagic and enterotoxigenic *E. coli* which may be treated in accordance with this invention are provided in Table 1 hereinbelow.

TABLE 1

| Pathogenic *E. coli* Serotypes (Group and Associated Serotypes) |
|---|
| Enterotoxigenic (ETEC) |
| O6:H16; O8:NM; O8:H9; O11:H27; O15:H11; O20:NM; O25:NM; O25:H42; O27:H7; O27:H20; O63:H12; O78:H11; O78:H12; O85:H7; O114:H21; O115:H21; O126:H9; O128ac:H7; O128ac:H12; O128ac:H21; O148:H28; O149:H4; O159:H4; O159:H20; O166:H27; and O167:H5 |
| Enterohemorrhagic (EHEC) |
| O1:NM; O2:H5; O2:H7; O4:NM; O4:H10; O5:NM; O5:H16; 06:H1; O18:NM; O18:H7; O25:NM; O26:NM; O26:H11; O26:H32; O8:H21; O39:H4; O45:H2; O50:H7; O55:H7; 055:H10; O82:H8; O84:H2; O91:NM; O91:H21; O103:H2; O111:NM; O111:H8; O111:H30; O111:H34; O113:H7; O113:H21; O114:H48; O115:H10; O117:H4; O118:H12; O118:H30; O121:NM; O121:H19; O125:NM; O125:H8; O126:NM; O126:H8; O128:NM; O128:H2; O128:H8; O128:H12; O128:H25; O145:NM; O125:H25; O146:H21; O153:H25; O157:NM; O157:H7; O163:H19; O165:NM; O165:19; and O165:H25 |

Many Shigella species produce shiga toxin and thus the method of the invention may be used for the treatment of a variety of Shigella species. Due to the incidence and severity of infections therewith, the method is particularly suited for the treatment of infections caused by *S. dysenteriae, S. sonnei, S. boydii*, and *S. flexneri*.

Without wishing to be bound by theory, the swainsonine compounds are believed to inhibit Golgi mannosidase II activity, thereby interfering with the expression of fully functional cell surface receptors for the bacterial enterotoxins. Thus, the cells of the treated animals exhibit significantly reduced binding of the enterotoxin relative to untreated or normal cells. In the case of infections by Shigella species or enterohemorrhagic *E. coli*, it is believed that protection may be the result of the modification of either or both of the glycolipid receptors globotriaosylceramide ($GB_3$ or $GB_4$) on the epithelial or other cell surfaces, or a second, low affinity shiga toxin binding site. The mechanism of this modification may be an interruption in the translocation process of the receptor from the site of synthesis to the outer cell membrane surface, or the synthesis of a receptor having significantly reduced toxin binding affinity. Animal host cells expressing cell surface receptors which may be effectively modified include but are not limited to epithelial (endothelial) cells of the gastrointestinal tract, glomerular cells of the kidney, endothelial cells of the mesenteric vasculature, and cerebral endothelial cells.

A variety of swainsonine compounds are suitable for use in the method of this invention, including swainsonine, derivatives of swainsonine, and salts of swainsonine or its derivatives. A number of such swainsonine compounds have been described in the prior art and may be used herein. By way of example, suitable swainsonine compounds include but are not limited to those disclosed by Tropper et al. (U.S. Pat. No. 6,051,711), Shah et al. (U.S. Pat. No. 6,048,870), Carver et al. (U.S. Pat. No. 5,962,467), Pearson et al. (U.S. Pat. No. 6,262,065), and Dime (U.S. Pat. No. 5,466,809), the contents of each of which are incorporated by reference herein.

As used herein, the term swainsonine compounds is therefore defined to include swainsonine, its salts, swainsonine derivatives, and their salts. Swainsonine derivatives are further defined as biologically effective molecules which retain the same indolizidine alkaloid base molecule as swainsonine wherein one or more of the 1–3 or 5–9 carbons contain additional or different (i.e., substituted) chemical moieties which are not normally part of swainsonine. The term "biologically effective" is also defined herein as effective for the inhibition of activity of α-D-mannosidases, specifically Golgi mannosidase II, and thereby effective for inhibiting the expression of fully functional enterotoxin receptors on the cell surfaces of the subject animal and consequently inhibiting the binding of the enterotoxins to the cell surfaces. As described above, this inhibition of functional receptors may be the result of the prevention or reduction of expression of receptors for the toxins on the cell surface, or receptors on the cell surface may be expressed but which receptors exhibit significantly reduced affinity for the toxins relative to an untreated control. Efficacy of swainsonine derivatives or their salts may be presumptively determined by measuring the inhibition of Jack Bean α-mannosidase. Mannosidase inhibition may also be measured by a toxin binding assay with toxin binding cells such as Vero cells, which are treated with the swainsonine compound as described in Example 1 herein. Briefly, a reduction in toxin toxicity against Vero cells treated with the swainsonine compounds relative to an untreated control reflects the ability of the compound to effectively inhibit the expression of functional toxin binding sites.

Treatment of a subject animal with the swainsonine compound to inhibit the binding of enterotoxins to the epithelial cells of the gastrointestinal tract is preferably initiated as soon as possible after the diagnosis of infection with one of the toxin-producing enteric bacterial pathogens. Depending upon the subject animal, this diagnosis is generally determined after the recognition of one or more symptoms associated with this infection. Such symptoms include, for example: diarrhea, particularly bloody diarrhea, abdominal cramping (in humans), blood in the stool, edema, central nervous system disorders, hemolytic uremic syndrome (in humans), rectal prolapse, detection of a toxin-producing bacterium in the patient's stool or bodily fluids; ingestion of food suspected of containing a toxin-producing bacterium; or close contact with an animal known to have a bacterial infection. In a preferred embodiment, the swainsonine compound is administered to the animal prior to organ involvement other than involvement of the intestine. In any event, the diagnosis of infection with one of the enteric toxin-producing bacterial pathogens is preferably subsequently confirmed by laboratory evaluation of stool specimens.

In an alternative preferred embodiment, the swainsonine compound may be administered prophylactically to an animal exposed to the toxin-producing enteric bacterial pathogens to prevent or alleviate the manifestation of symptoms of a subsequent infection. For example, prophylactic treatment of an animal may be initiated following the ingestion of food or water suspected of containing the toxin-producing bacteria, after exposure to an animal known to have an infection with one of the toxin-producing bacteria, or after exposure to an environment (e.g., feces) contaminated with the toxin-producing bacteria. This embodiment is particularly suited for use in veterinary applications, where the swainsonine compounds may be administered prophylactically to animals which are characteristically susceptible to infection with one or more of the toxin-producing enteric bacterial pathogens. For instance, piglets are particularly susceptible to the development of neonatal scours after birth, and later to post-weaning edema, each caused by enterotoxin-producing *E. coli*, and resulting in high levels of mortality. Thus, in a particularly preferred embodiment, these infections may be treated prior to the development of symptoms by administration of the swainsonine compounds to piglets during the period from about birth to about 1 week old, and/or during the period from about 17 to 28 days old, respectively.

Swainsonine itself may become toxic to an animal when administered over prolonged periods of time, even at recognized pharmacological levels [Stegelmeier et al., 2001, The clinical and morphologic changes of intermittent locoweed (*Oxytropis sericea*) poisoning in sheep, Proc. 6$^{th}$ Intl. Symp. Poisonous Plants, Glasgow, UK]. The specific length of treatment before swainsonine toxicity is evidenced will vary with the particular animal and the dose of the swainsonine compound. In most applications it is envisioned that swainsonine administration should not extend beyond about two weeks, although preferred treatment periods may be shortened to as little as about one week when administering high doses, or as long as about three weeks when administering low doses as described hereinbelow.

The method of the invention may be practiced with any animal susceptible to the toxins produced by any of the above-mentioned toxin-producing enteric pathogens, and particularly for those animals susceptible to the heat labile or heat stable toxins of enterotoxigenic *E. coli* (ETEC), and most particularly shiga toxins produced by Shigella species and enterohemorrhagic *E. coli*. The invention may therefore be practiced with a variety of animals, including, but not limited to swine, bovine, and primates, and particularly pigs and humans. Also without being limited thereto, the method may be used for the treatment of newborn, young or adult animals having normally functioning immune systems, and animals which are not immunocompromised but which are immunocompetent.

In use, the swainsonine compounds are preferably administered orally to the subject animal, although the compounds may also be administered by alternative routes such as parenterally. Typically, the compounds will be introduced into the alimentary tract by combining with the animal's feed or water, followed by oral ingestion thereof. It is also understood that the compounds may be administered separately or in combination with other conventional treatments.

The swainsonine compounds are administered in an amount effective to inhibit the binding of the enterotoxin to receptors on the cell surfaces of the subject animal. An effective amount is defined herein as that amount which will significantly reduce or eliminate the binding of a toxin produced by the target enteric bacterial pathogen to cell surface receptors in a treated animal relative to an untreated control animal. As noted above, this reduction in toxin binding may be due to a reduction of the expression of receptors on the cell surfaces for the toxin, or from a reduction in the affinity of receptors on the cell surface for the toxins. The inhibition of these functional cell surface receptors may be demonstrated by a significant reduction in the severity or pathogenicity of infection in comparison with untreated control animals. Suitable amounts may be readily determined by the practitioner skilled in the art, and will vary with the specific subject animal, duration of treatment, and swainsonine compound. Without being limited thereto, suitable daily doses of swainsonine are typically greater than about 5 ng/kg and less than or equal to about 10 mg/kg of body weight of the treated animal, preferably greater than about 10 ng/kg and less than or equal to about 10 mg/kg of body weight, and most preferably greater than about 10 ng/kg and less than or equal to about 1 mg/kg of body weight. The use of lower doses is particularly preferred for prolonged periods of treatment.

Although pure or substantially pure swainsonine compounds may be administered to the animals directly, in an optional yet preferred embodiment they are provided in the animal's feed (i.e., food) or drink such as water. Alternatively, the compounds may be further formulated with a conventional inert carrier or pharmaceutically acceptable carrier to facilitate administration. For example, without being limited thereto, all or a portion of the compounds may be encapsulated using techniques conventional in the art, or the compounds may also be formulated with saline, lactose or skim milk, or combined with a small amount of feed or water for use as a premix. Adjuvants conventional in the art for the treatment of the animals, including those for the treatment of enteropathogens, may also be formulated with the compounds. Suitable adjuvants include but are not limited to vaccines, antitoxins, deworming agents, or therapeutic antibiotics. In a particularly preferred embodiment, the swainsonine compounds are administered in combination with electrolytes conventional in the art for the treatment of bacterial enteric diseases. Non-therapeutic levels of antibiotics may also be administered to the animals as is conventional in the art.

The following examples are intended only to further illustrate the invention and are not intended to limit the scope of the invention which is defined by the claims.

EXAMPLE 1

This experiment was conducted to demonstrate that swainsonine regulates the expression of $GB_3$ and/or a second, low affinity shiga toxin binding site.

Materials and Methods: The supernatant from an overnight culture of ST1 and St2 producing *E. coli* O157:H7 was tested for activity against Vero cells in continuous culture using a microtiter LDH assay kit. Vero cells were seeded into the wells of a 96 well microtiter plate at a concentration of $10^4$ cells/well. For those wells in which the protective effects of swainsonine were evaluated, those cells were co-incubated with swainsonine during the 24 h establishment period. After establishment, the Vero cells were incubated overnight with either dilutions of shiga toxins (ST1 and ST2 from the *E. coli O*157:H7), shiga toxins plus swainsonine, or the appropriate control. LDH activity was assayed 24 h after the addition of shiga toxins.

Results: No toxic effects were observed in the swainsonine control wells when co-incubation occurred at levels as high as 5 $\mu$g/well. When cells were incubated with a 1/16 dilution of shiga toxins and 2.5 $\mu$g of swainsonine, LDH release levels were reduced by approximately 50% with respect to control. A reduction of 22% with respect to control was noted in wells incubated with the 2.5 $\mu$g of swainsonine and 1/8 dilution of toxin. A protective effect from co-incubation with swainsonine was observed at concentrations as low as 0.012 $\mu$g/well. These results indicate that co-incubation of Vero cells with swainsonine confers a significant degree of protection from shiga toxin activity.

EXAMPLE 2

This experiment was conducted to demonstrate that swainsonine may reduce manifestation of disease in piglets experimentally infected with *E. coli* O157:H7. The experimental challenge model used was developed by Nystrom et al. (2000*, Escherichia coli* O157:H7 Causes More-Severe Systemic Disease in Suckling Piglets than in Colostrum-Deprived Neonatal Piglets, Infect. Immun., 68: 2356–2358) and presents a very severe challenge to neonatal piglets with very little likelihood of any piglets surviving.

Materials and Methods: A pregnant sow was farrowed at the Southern Plains Agricultural Research Center. Piglets from this sow were randomly allotted to treatment soon after farrowing. In this study, commercially available swainsonine extracted from *Rhizoctonia leguminicola* was used.

Experimental infection and swainsonine treatment: Piglets farrowed from the sow were orally challenged with 1 ml of a stock cell suspension containing $10^{10}$ CFU of a streptomycin resistant *E. coli* O157:H7 strain 86-24. The stock cells suspensions will be prepared previously by centrifuging an overnight grown culture (grown in TSB) containing approximately $10^9$ CFU at 10,000×g for 20 min and then resuspending the cell pellet in $1/10^{th}$ volume of half strength TSB containing 10% glycerol. The resuspended suspensions were stored in 15 ml aliquots at −70° C. until use. Swainsonine treatments were administered orally as 0.5 ml suspensions of 1 mg swainsonine/ml in normal saline, with first administration given upon observation of first signs of clinical disease (severe diarrhea, shivering, severe tremors, hind-leg weakness, sprayleg, paralysis, lateral, sternal or dorsal recumbency, paddling, squealing or convulsions).

Results: The six pigs farrowed from the sow were challenged with 1 ml of a stock cell suspension containing $10^{10}$ CFU of a streptomycin resistant *E. coli* O157:H7 strain 86-24 at 3 h of age. These pigs were watched at frequent intervals for symptoms of disease which began 20 h after oral challenge. At this time, 3 of the 6 piglets from this litter were each orally administered 0.5 ml of a 1 mg swainsonine/ml normal saline solution. These same three piglets were treated again at 39 h post challenge (so all in all, the piglets received 1 mg swainsonine which is equivalent to 1 mg/kg BW). Manifestation of disease progressed very rapidly over the next several days for the non-swainsonine treated pigs, with one pig dying by 39 h post challenge, another at 63 h post challenge and the remaining non-swainsonine-treated pig being humanely euthanized at 68 h post challenge (pig was moribund). In the case of the swainsonine-treated pigs, progression of disease was less rapid and for all except one, much less severe. Two of the swainsonine-treated pigs were recovering from the disease by 68 h post challenge, the other was euthanized for humane reasons at 68 h post challenge. Preliminary results from another litter showed no adverse effects when piglets (n=3) not challenged with *E. coli* O157:H7 but were orally administered swainsonine as above.

It is understood that the foregoing detailed description is given merely by way of illustration and that modifications and variations may be made therein without departing from the spirit and scope of the invention.

We claim:

1. A method for treating enteric infections in an animal comprising administering a swainsonine compound to an immunocompetent animal exposed to or infected with a toxin-producing enteric pathogen selected from the group consisting of Shigella species, enterohemorrhagic *E. coli*, and enterotoxigenic *E. coli*, wherein said swainsonine compound is administered in an amount effective to inhibit the binding of said toxin to the surfaces of cells of said animal.

2. The method of claim 1 wherein said swainsonine compound is selected from the group consisting of swainsonine, swainsonine derivatives, and pharmaceutically acceptable salts thereof.

3. The method of claim 1 wherein said swainsonine compound comprises swainsonine.

4. The method of claim 2 wherein said toxin is a shigatoxin and said toxin producing enteric pathogen is selected from the group consisting of Shigella species and enterohemorrhagic *E. coli.*

5. The method of claim 1 wherein said swainsonine compound is administered orally to said animal.

6. The method of claim 5 wherein said swainsonine compound is formulated in a composition with a carrier.

7. The method of claim 6 wherein said carrier comprises a pharmaceutically acceptable carrier.

8. The method of claim 5 wherein said administering comprises providing said swainsonine compound in combination with water for said animal.

9. The method of claim 5 wherein said administering comprises providing said swainsonine compound in combination with feed for said animal.

10. The method of claim 1 wherein said amount of said swainsonine compound is greater than about 5 ng/kg and less than or equal to about 10 mg/kg of body weight of said animal.

11. The method of claim 1 wherein said amount of said swainsonine compound is greater than about 10 ng/kg and less than or equal to about 10 mg/kg of body weight of said animal.

12. The method of claim 1 wherein said amount of said swainsonine compound is greater than about 10 ng/kg and less than or equal to about 1 mg/kg of body weight of said animal.

13. The method of claim 1 wherein the immune system of said animal functions normally.

14. The method of claim 1 wherein said animal is selected from the group consisting of primates, bovine, and swine.

15. The method of claim 1 wherein said animal is selected from the group consisting of primates and swine.

16. The method of claim 1 wherein said animal is infected with said toxin-producing enteric pathogen selected from the group consisting of Shigella species, enterohemorrhagic *E. coli*, and enterotoxigenic *E. coli.*

17. The method of claim 1 wherein said animal is selected from the group consisting of bovine, and swine.

18. The method of claim 1 wherein said animal is a swine.

19. A method for treating enteric infections in an animal comprising administering a swainsonine compound to an animal exposed to or infected with a toxin-producing enteric pathogen selected from the group consisting of Shigella species, enterohemorrhagic *E. coli*, and enterotoxigenic *E. coli*, wherein said swainsonine compound is administered in an amount effective to inhibit the binding of said toxin to the surfaces of cells of said animal, and further wherein the immune system of said animal functions normally.

* * * * *